United States Patent [19]
Armistead et al.

[11] Patent Number: 5,807,876
[45] Date of Patent: Sep. 15, 1998

[54] INHIBITORS OF IMPDH ENZYME

[75] Inventors: David M. Armistead, Maynard; Michael C. Badia, Bedford; Guy W. Bemis, Arlington; Randy S. Bethiel, Allston; Catharine A. Frank, Marlborough; Perry M. Novak, Milford; Steven M. Ronkin, Watertown; Jeffrey O. Saunders, Acton, all of Mass.

[73] Assignee: Vertex Pharmaceuticals Incorporated, Cambridge, Mass.

[21] Appl. No.: 636,361

[22] Filed: Apr. 23, 1996

[51] Int. Cl.$^6$ .................. A61K 31/42; C07D 263/34; C07D 413/00
[52] U.S. Cl. ............................... 514/374; 548/236
[58] Field of Search .............................. 548/236; 514/374

[56] References Cited

U.S. PATENT DOCUMENTS

| | | | |
|---|---|---|---|
| 5,380,879 | 1/1995 | Sjogren | 549/310 |
| 5,444,072 | 8/1995 | Patterson et al. | 514/320 |
| 5,569,654 | 10/1996 | Armour et al. | 514/221 |

FOREIGN PATENT DOCUMENTS

| | | | |
|---|---|---|---|
| WO 94/01105 | 1/1994 | WIPO | A61K 31/35 |
| WO 94/12184 | 6/1994 | WIPO | A61K 31/535 |

OTHER PUBLICATIONS

J.A. Huete–Pérez et al., "Identification of the IMP Binding Site in the IMP Dehydrogenase From *Tritrichomonas Foetus*", *Biochemistry*, 34, pp. 13889–13894 (Oct., 1995).

C.R. Gregory et al., "Treatment With Rapamycin and Mycophenolic Acid Reduces Arterial Intimal Thickening Produced by Mechanical Injury and Allows Endothelial Replacement", *Transplantation*, 59(5), pp. 655–661 (Mar., 1995).

G.M. Makara et al. "Nuclear Magnetic Resonance and Molecular Modeling Study on Mycophenolic Acid: Implications for Binding to Inosine Monophosphate Dehydrogenase", *J. Med. Chem.* 39, pp. 1236–1242 (Mar., 1996).

C. Montero et al., "Demonstrations of Induction of Erythocyte Inosine Monophosphate Dehydrogenase Acitivity in Ribavirin–Treated Patients Using a High Performance Liquid Chromatography Linked Method", *Clinica Chimica Acta*, 238, pp. 169–178 (Aug., 1995).

R.E. Morris, "New Small Molecule Immunosuppressants for Transplantation: Review of Essential Concepts", *The Journal of Heart and Lung Transplantation*, 12, pp. S–275–S–286 (1993).

F.G. Whitby et al., "Preliminary X–Ray Crystallographic Analysis of *Tritrichonas foetus* Inosine–5–Monophosphate Dehydrogenase", *Proteins: Structure, Function and Genetics*, 23, pp. 598–603 (1995).

*Primary Examiner*—Mukund J. Shah
*Assistant Examiner*—Bruck Kifle
*Attorney, Agent, or Firm*—Fish & Neave; James F. Haley, Jr.; N. Govindaswamy

[57] ABSTRACT

The present invention relates to a novel class of compounds which are IMPDH inhibitors. This invention also relates to pharmaceutical compositions comprising these compounds. The compounds and pharmaceutical compositions of this invention are particularly well suited for inhibiting IMPDH enzyme activity and consequently, may be advantageously used as agents for immunosuppression. This invention also relates to methods for inhibiting the activity of IMPDH using the compounds of this invention and related compounds.

21 Claims, No Drawings

INHIBITORS OF IMPDH ENZYME

TECHNICAL FIELD OF THE INVENTION

The present invention relates to a novel class of compounds which inhibit IMPDH. This invention also relates to pharmaceutical compositions comprising these compounds. The compounds and pharmaceutical compositions of this invention are particularly well suited for inhibiting IMPDH enzyme activity and consequently, may be advantageously used as therapeutic agents for IMPDH mediated processes. This invention also relates to methods for inhibiting the activity of IMPDH using the compounds of this invention and related compounds.

BACKGROUND OF THE INVENTION

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH; EC 1.1.1.205) is an enzyme involved in the de novo synthesis of guanosine nucleotides. IMPDH catalyzes the NAD-dependent oxidation of inosine-5'-monophosphate (IMP) to xanthosine-5'-monophosphate (XMP)[Jackson R. C. et. al., *Nature*, 256, pp. 331–333, (1975)].

IMPDH is ubiquitous in eukaryotes, bacteria and protozoa [Y. Natsumeda & S. F. Carr, *Ann. N.Y. Acad.*, 696, pp. 88–93 (1993)]. The prokaryotic forms share 30–40% sequence identity with the human enzyme. Regardless of species, the enzyme follows an ordered Bi-Bi reaction sequence of substrate and cofactor binding and product release. First, IMP binds to IMPDH. This is followed by the binding of the cofactor NAD. The reduced cofactor, NADH, is then released from the product, followed by the product, XMP [S. F. Carr et al., *J. Biol. Chem.*, 268, pp. 27286–90 (1993); E. W. Holmes et al., *Biochim. Biophys. Acta*, 364, pp. 209–217 (1974)]. This mechanism differs from that of most other known NAD-dependent dehydrogenases, which have either a random order of substrate addition or require NAD to bind before the substrate.

Two isoforms of human IMPDH, designated type I and type II, have been identified and sequenced [F. R. Collart and E. Huberman, *J. Biol. Chem.*, 263, pp. 15769–15772, (1988); Y. Natsumeda et. al., *J. Biol. Chem.*, 265, pp. 5292–5295, (1990)]. Each is 514 amino acids, and they share 84% sequence identity. Both IMPDH type I and type II form active tetramers in solution, with subunit molecular weights of 56 kDa [Y. Yamada et. al., *Biochemistry*, 27, pp. 2737–2745 (1988)].

The de novo synthesis of guanosine nucleotides, and thus the activity of IMPDH, is particularly important in B and T-lymphocytes. These cells depend on the de novo, rather than salvage pathway to generate sufficient levels of nucleotides necessary to initiate a proliferative response to mitogen or antigen [A. C. Allison et. al., *Lancet II*, 1179, (1975) and A. C. Allison et. al., *Ciba Found. Symp.*, 48, 207, (1977)]. Thus, IMPDH is an attractive target for selectively inhibiting the immune system without also inhibiting the proliferation of other cells.

Immunosuppression has been achieved by inhibiting a variety of enzymes including for example, the phosphatase calcineurin (inhibited by cyclosporin and FK-506); dihydroorotate dehydrogenase, an enzyme involved in the biosynthesis of pyrimidines (inhibited by leflunomide and brequinar); the kinase FRAP (inhibited by rapamycin); and the heat shock protein hsp70 (inhibited by deoxyspergualin). [See B. D. Kahan, *Immunological Reviews*, 136, pp. 29–49 (1993); R. E. Morris, *The Journal of Heart and Lung Transplantation*, 12(6), pp. S275–S286 (1993)].

Inhibitors of IMPDH are also known. U.S. Pat. Nos. 5,380,879 and 5,444,072 and PCT publications WO 94/01105 and WO 94/12184 describe mycophenolic acid (MPA) and some of its derivatives as potent, uncompetitive, reversible inhibitors of human IMPDH type I ($K_i$=33 nM) and type II ($K_i$=9 nM). MPA has been demonstrated to block the response of B and T-cells to mitogen or antigen [A. C. Allison et. al., *Ann. N.Y. Acad. Sci.*, 696, 63, (1993).

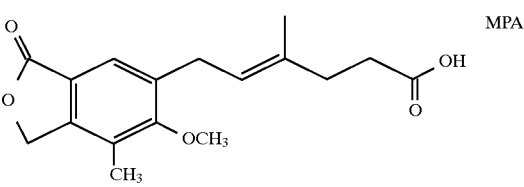

Immunosuppressants, such as MPA, are useful drugs in the treatment of transplant rejection and autoimmune diseases. [R. E. Morris, *Kidney Intl.*, 49, Suppl. 53, S-26, (1996)]. However, MPA is characterized by undesirable pharmacological properties, such as gastrointestinal toxicity and poor bioavailability. [L. M. Shaw, et. al., *Therapeutic Drug Monitoring*, 17, pp. 690–699, (1995)].

Nucleoside analogs such as tiazofurin, ribavirin and mizoribine also inhibit IMPDH [L. Hedstrom, et. al. *Biochemistry*, 29, pp. 849–854 (1990)]. These compounds, which are competitive inhibitors of IMPDH, suffer from lack of specificity to this enzyme.

Mycophenolate mofetil, a prodrug which quickly liberates free MPA in vivo, was recently approved to prevent acute renal allograft rejection following kidney transplantation. [L. M. Shaw, et. al., *Therapeutic Drug Monitoring*, 17, pp. 690–699, (1995); H. W. Sollinger, *Transplantation*, 60, pp. 225–232 (1995)]. Several clinical observations, however, limit the therapeutic potential of this drug. [L. M. Shaw, et. al., *Therapeutic Drug Monitoring*, 17, pp. 690–699, (1995)]. MPA is rapidly metabolized to the inactive glucuronide in vivo. [A. C., Allison and E. M. Eugui, *Immunological Reviews*, 136, pp. 5–28 (1993)]. The glucuronide then undergoes enterohepatic recycling causing accumulation of MPA in the gastrointestinal tract where it cannot exert its IMPDH inhibitory activity on the immune system. This effectively lowers the drug's in vivo potency, while increasing its undesirable gastrointestinal side effects.

It is also known that IMPDH plays a role in other metabolic events. Increased IMPDH activity has been observed in rapidly proliferating human leukemic cell lines and other tumor cell lines, indicating IMPDH as a target for anti-cancer as well as immunosuppressive chemotherapy [M. Nagai et. al., *Cancer Res.*, 51, pp. 3886–3890, (1991)]. IMPDH has also been shown to play a role in the proliferation of smooth muscle cells, indicating that inhibitors of IMPDH, such as MPA or rapamycin, may be useful in preventing restenosis or other hyperproliferative vascular diseases [C. R. Gregory et al., *Transplantation*, 59, pp. 655–61 (1995); PCT publication WO 94/12184; and PCT publication WO 94/01105].

Additionally, IMPDH has been shown to play a role in viral replication in some viral cell lines. [S. F. Carr, *J. Biol. Chem.*, 268, pp. 27286–27290 (1993)]. Analogous to lymphocyte and tumor cell lines, the implication is that the de novo, rather than the salvage, pathway is critical in the process of viral replication.

Thus, there remains a need for potent IMPDH inhibitors with improved pharmacological properties. Such inhibitors would have therapeutic potential as immunosuppressants, anti-cancer agents, anti-vascular hyperproliferative agents and anti-viral agents. Specifically, such compounds may be used in the treatment of transplant rejection and autoimmune diseases, such as rheumatoid arthritis, multiple sclerosis, juvenile diabetes, asthma, inflammatory bowel disease, as well as in the treatment of cancer and tumors, such as lymphomas and leukemia, vascular diseases, such as restenosis, and viral replication diseases, such as retroviral diseases and herpes.

SUMMARY OF THE INVENTION

The present invention provides compounds, and pharmaceutically acceptable derivatives thereof, that are useful as inhibitors of IMPDH. These compounds can be used alone or in combination with other therapeutic or prophylactic agents, such as anti-virals, anti-inflammatory agents, antibiotics, and immunosuppressants for the treatment or prophylaxis of transplant rejection and autoimmune disease. Additionally, these compounds are useful, alone or in combination with other agents, as therapeutic and prophylactic agents for antiviral, anti-tumor, anti-cancer, immunosuppressive chemotherapy and restenosis therapy regimens.

The invention also provides pharmaceutical compositions comprising the compounds of this invention, as well as multi-component compositions comprising additional IMPDH compounds together with an immunosuppressant. The invention also provides methods of using the compounds of this invention, as well as other related compounds, for the inhibition of IMPDH.

The compounds of this invention, as well as those used in the methods of this invention demonstrate a different metabolic profile than MPA and its derivatives. Because of this difference, methods of this invention and the compounds used therein may offer advantages as therapeutics for IMPDH mediated disease. These advantages include increased overall therapeutic benefit and reduction in deleterious side effects.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Ac | acetyl |
| Me | methyl |
| Et | ethyl |
| Bn | benzyl |
| CDI | carbonyldiimidazole |
| DIEA | diisopropylethylamine |
| DMAP | dimethylaminopyridine |
| DMF | dimethylformamide |
| DMSO | dimethylsulfoxide |
| EDC | 1-(3-dimethylaminopropyl)-3-ethylcarbodiimide hydrochloride |
| EtOAc | ethyl acetate |
| THF | tetrahydrofuran |

The following terms are employed herein:

Unless expressly stated to the contrary, the terms "—SO$_2$—" and "—S(O)$_2$—" as used herein refer to a sulfone or sulfone derivative (i.e., both appended groups linked to the S), and not a sulfinate ester.

The terms "halo" or "halogen" refer to a radical of fluorine, chlorine, bromine or iodine.

The term "immunosuppressant" refers to a compound or drug which possesses immune response inhibitory activity. Examples of such agents include cyclosporin A, FK506, rapamycin, leflunomide, deoxyspergualin, prednisone, azathioprine, mycophenolate mofetil, OKT3, ATAG and mizoribine.

IMPDH-mediated disease refers to any disease state in which the IMPDH enzyme plays a regulatory role in the metabolic pathway of that disease. Examples of IMPDH-mediated disease include transplant rejection and autoimmune diseases, such as rheumatoid arthritis, multiple sclerosis, juvenile diabetes, asthma, and inflammatory bowel disease, as well as cancer, viral replication diseases and vascular diseases.

The term "treating" as used herein refers to the alleviation of symptoms of a particular disorder in a patient or the improvement of an ascertainable measurement associated with a particular disorder. As used herein, the term "patient" refers to a mammal, including a human.

The term "thiocarbamates" refers to compounds containing the functional group N—SO$_2$—O.

According to one embodiment, the invention provides methods of inhibiting IMPDH activity in a mammal comprising the step of administering to said mammal, a compound of formula I:

wherein:

A is selected from:
(C$_1$–C$_6$)-straight or branched alkyl, or (C$_2$–C$_6$)-straight or branched alkenyl or alkynyl; and A optionally comprises up to 2 substituents, wherein:
the first of said substituents, if present, is selected from R$^1$ or R$^3$, and
the second of said substituents, if present, is R$^1$;

B is a saturated, unsaturated or partially saturated monocyclic or bicyclic ring system optionally comprising up to 4 heteroatoms selected from N, O, or S and selected from the formulae:

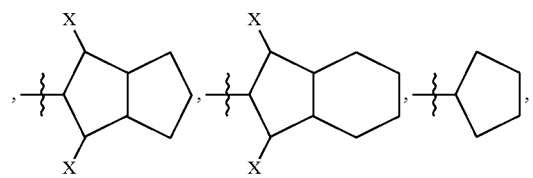

-continued

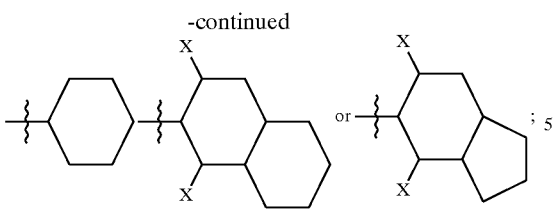

wherein each X is the number of hydrogen atoms necessary to complete proper valence;
and B optionally comprises up to 3 substituents,
wherein:
  the first of said substituents, if present, is selected from $R^1$, $R^2$, $R^4$ or $R^5$,
  the second of said substituents, if present, is selected from $R^1$ or $R^4$, and
  the third of said substituents, if present, is $R^1$; and
D is selected from C(O), C(S), or $S(O)_2$; wherein:
  each $R^1$ is independently selected from 1,2-methylenedioxy, 1,2-ethylenedioxy, $R^6$ or $(CH_2)_n$—Y;
  wherein n is 0, 1 or 2; and
  Y is selected from halogen, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;
  each $R^2$ is independently selected from $(C_1-C_4)$-straight or branched alkyl, or $(C_2-C_4)$-straight or branched alkenyl or alkynyl; and each $R^2$ optionally comprises up to 2 substituents, wherein:
    the first of said substituents, if present, is selected from $R^1$, $R^4$ and $R^5$, and
    the second of said substituents, if present, is $R^1$;
$R^3$ is selected from a monocyclic or a bicyclic ring system consisting of 5 to 6 members per ring, wherein said ring system optionally comprises up to 4 heteroatoms selected from N, O, or S, and wherein a $CH_2$ adjacent to any of said N, O, or S heteroatoms is optionally substituted with C(O); and each $R^3$ optionally comprises up to 3 substituents, wherein:
  the first of said substituents, if present, is selected from $R^1$, $R^2$, $R^4$ or $R^5$,
  the second of said substituents, if present, is selected from $R^1$ or $R^4$, and
  the third of said substituents, if present, is $R^1$;
each $R^4$ is independently selected from $OR^5$, $OC(O)R^6$, $OC(O)R^5$, $OC(O)OR^6$, $OC(O)OR^5$, $OC(O)N(R^6)_2$, $OP(O)(OR^6)_2$, $SR^6$, $SR^5$, $S(O)R^6$, $S(O)R^5$, $SO_2R^6$, $SO_2R^5$, $SO_2N(R^6)_2$, $SO_2NR^5R^6$, $SO_3R^6$, $C(O)R^5$, $C(O)OR^5$, $C(O)R^6$, $C(O)OR^6$, $NC(O)C(O)R^6$, $NC(O)C(O)R^5$, $NC(O)C(O)OR^6$, $NC(O)C(O)N(R^6)_2$, $C(O)N(R^6)_2$, $C(O)N(OR^6)R^6$, $C(O)N(OR^6)R^5$, $C(NOR^6)R^6$, $C(NOR^6)R^5$, $N(R^6)_2$, $NR^6C(O)R^1$, $NR^6C(O)R^6$, $NR^6C(O)R^5$, $NR^6C(O)OR^6$, $NR^6C(O)OR^5$, $NR^6C(O)N(R^6)_2$, $NR^6C(O)NR^5R^6$, $NR^6SO_2R^6$, $NR^6SO_2R^5$, $NR^6SO_2N(R^6)_2$, $NR^6SO_2NR^5R^6$, $N(OR^6)R^6$, $N(OR^6)R^5$, $P(O)(OR^6)N(R^6)_2$, and $P(O)(OR^6)_2$;
each $R^5$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^5$ optionally comprises up to 3 substituents, each of which, if present, is $R^1$;
each $R^6$ is independently selected from H, $(C_1-C_4)$-straight or branched alkyl, or $(C_2-C_4)$ straight or branched alkenyl; and each $R^6$ optionally comprises a substituent that is $R^7$;
$R^7$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^7$ optionally comprises up to 2 substituents independently chosen from H, $(C_1-C_4)$-straight or branched alkyl, $(C_2-C_4)$ straight or branched alkenyl, 1,2-methylenedioxy, 1,2-ethylenedioxy, or $(CH_2)_n$—Z;
wherein n is 0, 1 or 2; and
Z is selected from halogen, CN, $NO_2$, $CF_3$, $OCF_3$, OH, $S(C_1-C_4)$-alkyl, $SO(C_1-C_4)$-alkyl, $SO_2(C_1-C_4)$-alkyl, $NH_2$, $NH(C_1-C_4)$-alkyl, $N((C_1-C_4)$-alkyl$)_2$, $N((C_1-C_4)$-alkyl$)R^8$, COOH, $C(O)O(C_1-C_4)$-alkyl or $O(C_1-C_4)$-alkyl; and
$R^8$ is an amino protecting group; and
wherein any carbon atom in any A, $R^2$ or $R^6$ is optionally replaced by 0, S, SO, $SO_2$, NH, or $N(C_1-C_4)$-alkyl.

The term "substituted" refers to the replacement of one or more hydrogen radicals in a given structure with a radical selected from a specified group. When more than one hydrogen radical may be replaced with a substituent selected from the same specified group, the substituents may be either the same or different at every position.

The term "monocyclic or bicyclic ring system consisting of 5 to 6 members per ring" refers to 5 or 6 member monocyclic rings and 8, 9 and 10 membered bicyclic ring structures, wherein each bond in each ring may be possess any degree of saturation that is chemically feasible. When such structures contain substituents, those substituents may be at any position of the ring system, unless otherwise specified.

As specified, such ring systems may optionally comprise up to 4 heteroatoms selected from N, O or S. Those heteroatoms may replace any carbon atoms in these ring systems as long as the resulting compound is chemically stable.

The term "wherein each X is the number of hydrogen atoms necessary to complete proper valence" means that X is 0, 1 or 2 hydrogen atoms, depending upon the identity of the ring atom to which X is bound (C, N, O or S), the identity of the two adjacent ring atoms, and the nature of the bonds between the ring atom to which X is bound and the two adjacent ring atoms (single, double or triple bond). In essence, this definition is meant to exclude from X any substituents other than hydrogen.

The term "amino protecting group" refers to a suitable chemical group which may be attached to a nitrogen atom. The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reaaents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

According to another embodiment, the invention provides methods of inhibiting IMPDH in mammals by administering a compound of the formula (II):

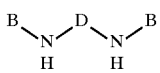

wherein B and D are as defined above.

More preferably, in methods employing the compounds of formulae (I) or (II), component B comprises from 0 to 2 substituents. According to an alternate embodiment, the invention provides methods for inhibiting IMPDH in a mammal employing compounds (I) or (II), wherein B comprises at least a single substituent selected from the group defined by $R^5$. Preferably, in this embodiment, B is a monocyclic aromatic ring containing at least one substituent which is also a monocyclic aromatic ring.

The present invention also provides compounds which are useful in inhibiting IMPDH. According to one embodiment, the IMPDH inhibitory compound has the formula (III):

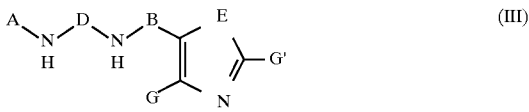

wherein A, B and D are as defined above; E is oxygen or sulfur; and G and G' are independently selected from $R^1$ or hydrogen.

According to an alternate embodiment, the invention provides a compound of the formula (IV):

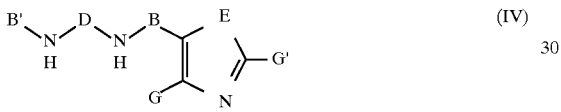

wherein B, D, E, G and G' are defined as above and B' is a saturated, unsaturated or partially saturated monocyclic or bicyclic ring system optionally comprising up to 4 heteroatoms selected from N, O, or S and selected from the formulae:

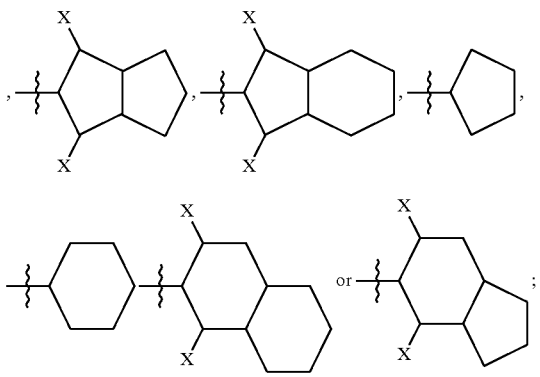

wherein each X is the number of hydrogen atoms necessary to complete proper valence; and B' optionally comprises up to 3 substituents, wherein:

the first of said substituents, if present, is selected from $R^1$, $R^2$, $R^4$ or $R^5$, the second of said substituents, if present, is selected from $R^1$ or $R^4$, and the third of said substituents, if present, is $R^1$; wherein X, $R^1$, $R^2$, $R^4$ and $R^5$ are defined as above.

Excluded from this invention are compounds of formula (IV) wherein B and B' are simultaneously unsubstituted phenyl and compounds wherein B is unsubstituted phenyl and B' is tri-chloro-, tri-bromo or tri-iodo phenyl.

Preferably, in compounds of formula (IV), B and B' are phenyl groups comprising at least one substituent each. These compounds are represented by formula (V):

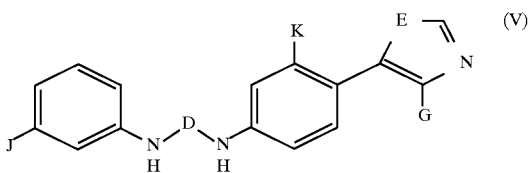

wherein K is selected from $R^1$ or $R^4$; and J is selected from $R^1$, $R^2$ or $R^4$.

Preferred compounds of formula (V) are those wherein E is oxygen; those wherein J is $NR^6C(O)R^5$ or $NR^6C(O)R^6$, preferably $NR^6C(O)R^6$ and more preferably $N(CH_3)C(O)R^6$; those wherein K is $(CH_2)_n$—Y, preferably $OCH_3$ (i.e., n is 0, Y is $OR^6$, and $R^6$ is $CH_3$); and those wherein G is hydrogen. More preferred compounds of formula (V) are those wherein:

E is oxygen

J is $NR^6C(O)R^5$ or $NR^6C(O)R^6$;

K is $(CH_2)_n$—Y; and

G is hydrogen.

Even more preferred compounds of formula (V) are those wherein:

E is oxygen

J is $NR^6C(O)R^6$;

K is $OCH_3$; and

G is hydrogen.

Most preferably in such compounds, J is $N(CH_3)C(O)R^6$.

Tables IA and IB list preferred individual compounds of the invention. Table II lists preferred compounds employed in the methods of this invention.

TABLE IA

| # | G | K | A |
|---|---|---|---|
| 1 | H | H | benzyl |

TABLE IB

| # | G | K | B' |
|---|---|---|---|
| 2 | H | H | 3-methoxyphenyl |
| 3 | H | H | 3-thienyl |
| 4 | H | H | 3,4-difluorophenyl |
| 5 | H | H | 2,5-dimethoxyphenyl |
| 6 | H | H | 3-methylthiophenyl |
| 7 | H | H | 3-bromophenyl |

TABLE IB-continued

| # | G | K | B' |
|---|---|---|-----|
| 8 | H | H | 3-cyanophenyl |
| 9 | H | H | 3-trifluoromethyl-4-chlorophenyl |
| 10 | H | H | 2-methyl-3-chlorophenyl |
| 11 | H | H | 2-methoxy-5-methylphenyl |
| 12 | H | H | 2-methoxyphenyl |
| 13 | H | H | 3-methoxyphenyl |
| 14 | H | H | 2,5-dimethoxyphenyl |
| 15 | H | H | 3-nitrophenyl |
| 16 | H | H | 4-nitrophenyl |
| 17 | H | H | 3-methylphenyl |
| 18 | H | H | 3-trifluoromethylphenyl |
| 19 | H | H | 2-trifluoromethylphenyl |
| 20 | H | H | 3-fluorophenyl |
| 21 | H | H | 4-phenoxyphenyl |
| 22 | H | H | 3-chlorophenyl |
| 23 | H | H | 3-chloro-4-fluorophenyl |
| 24 | H | H | 3-aminophenyl |
| 25 | H | H | 3-(hydroxymethyl)phenyl |
| 26 | H | H | 3-acetylenylphenyl |
| 27 | H | H | 3-hydroxyphenyl |
| 29 | H | H | 3-pyridinyl |
| 30 | H | H | 4-pyridinyl |
| 31 | H | H | 2-(5-methyl)thiazolyl |
| 39 | H | H | 3,4-ethylenedioxyphenyl |
| 40 | H | H | 3-methyl-4-nitrophenyl |
| 41 | H | H | 3-trifluoromethyl-4-nitrophenyl |
| 42 | H | 3-chloro | phenyl |
| 43 | H | 3-chloro | 3-methylphenyl |
| 44 | H | H | phenyl |
| 45 | H | 3-fluoro | phenyl |
| 46 | H | 3-fluoro | 3-methylphenyl |
| 47 | H | H | 3-carbomethoxymethylphenyl |
| 48 | H | H | 3-carboxyethylphenyl |
| 49 | H | H | 3-dimethylaminophenyl |
| 50 | H | H | 3-[2-(2-methyl)dioxolanyl]phenyl |
| 51 | H | H | 3-aminocarbonylphenyl |
| 53 | H | H | 3-(3-furanyl)-phenyl |
| 54 | H | H | 3-carboxymethylphenyl |
| 55 | H | 3-methoxy | 3-methylphenyl |
| 56 | H | 3-methoxy | 3-nitrophenyl |
| 57 | H | 3-chloro | 3-carbomethoxymethylphenyl |
| 58 | H | H | 3-amino-5-methylphenyl |
| 59 | H | 3-methoxy | 3-aminophenyl |
| 60 | H | 3-bromo | 3-methylphenyl |
| 61 | H | 3-chloro | 3-chloro-4-(5-oxazolyl)phenyl |
| 62 | H | 3-chloro | 4-(2-methylpyridyl) |
| 63 | H | 3-chloro | 3-carboxymethylphenyl |
| 64 | H | 3-bromo | 3-nitrophenyl |
| 65 | H | 3-bromo | 3-aminophenyl |
| 66 | H | H | 3-[5-(2-methylpyrimidinyl)]phenyl |
| 67 | H | H | 3-(5-oxazolyl)phenyl |
| 68 | H | 3-chloro | 2-thienyl |
| 69 | H | 3-chloro | 3-thienyl |
| 71 | H | 3-chloro | 3-methoxycarbamoyl-phenyl |
| 72 | H | 3-chloro | 3-acetamidophenyl |
| 73 | H | 3-chloro | 3-iodophenyl |
| 74 | H | 3-methyl | phenyl |
| 75 | H | 3-methyl | 3-methylphenyl |
| 76 | methyl | 3-chloro | 3-methylphenyl |
| 77 | methyl | H | 3-methylphenyl |
| 78 | H | 3-chloro | 3-nitrophenyl |
| 79 | H | 3-chloro | 3-aminophenyl |
| 80 | H | H | 3-(cyclohexylsulfamoyl)phenyl |
| 81 | H | H | 3-(methylsufamoyl)phenyl |
| 82 | H | H | 3-(phenylsufamoyl)phenyl |
| 83 | H | 3-methoxy | 3-benzyloxycarbamoyl-phenyl |
| 84 | H | 3-methoxy | 3-acetamidophenyl |
| 85 | H | 3-chloro | 4-(2-methyl)furanyl |
| 86 | H | 3-chloro | 5-(2-methyl)thienyl |
| 88 | H | 3-carbomethoxy | 3-methylphenyl |
| 89 | H | 3-carbomethoxy | 3-nitrophenyl |
| 91 | H | 3-chloro | 4-(2-nitro)thienyl |
| 92 | H | 3-chloro | 4-(2-hydroxyamino)thienyl |
| 93 | H | 3-chloro | 3-(N-methyl)trifluoroacetamido-phenyl |
| 94 | H | 3-chloro | 3-(methylamino)phenyl |
| 95 | H | 3-chloro | 4-(2-amino)thienyl |
| 96 | H | 3-methoxy | 3-trifluoroacetamidophenyl |
| 97 | H | 3-methoxy | 3-(N-methyl)trifluoroacetamido-phenyl |
| 98 | H | 3-methoxy | 3-(3'-picolyloxycarbamoyl)phenyl |
| 99 | H | 3-methoxy | 3-(phenoxycarbamoyl)phenyl |
| 100 | H | 3-methoxy | 3-difluoroacetamidophenyl |
| 101 | H | 3-acetoxymethyl | 3-methylphenyl |
| 102 | H | 3-hydroxymethyl | 3-methylphenyl |
| 104 | H | H | 3-nitro-4-fluorophenyl |
| 105 | H | 3-methoxy | 3-(aminomethyl)phenyl [*TFA] |
| 106 | H | 3-methoxy | 5-(N-acetoxy)indolinyl |
| 107 | H | 3-methoxy | 3-(N-methyl)acetamidophenyl |
| 108 | H | 3-methoxy | 3-[(2-oxo-2-(3,4,5-tri-methoxyphenyl)acetyl)amino]phenyl |
| 109 | H | 3-amino | 3-methylphenyl |
| 110 | H | 3-methoxy | 3-benzamidophenyl |
| 111 | H | 3-methoxy | 3-phenylacetamidophenyl |
| 112 | H | 3-methoxy | 3-phenylureidophenyl |
| 113 | H | 3-methoxy | 3-(t-butoxycarbamoyl methyl)phenyl |
| 114 | H | 3-methoxy | 3-(cyclopentylacetamido)phenyl |
| 115 | H | 3-methoxy | 3-methylphenyl |

TABLE II

| # | Q¹ | Q² | B |
|---|----|----|---|
| 28 | 3-methoxy | 4-methoxy | 3-methylphenyl |
| 32 | 3-nitro | H | 3-methylphenyl |
| 33 | 4-cyano | H | 3-methylphenyl |
| 34 | 3-methoxy | 4-methoxy | 3-bromophenyl |
| 35 | 3-methoxy | 4-methoxy | 2-methoxy-5-chlorophenyl |
| 36 | 3-methoxy | 4-methoxy | 3-fluorophenyl |
| 37 | 3-methoxy | 4-methoxy | 3-ethylphenyl |
| 38 | 3-methoxy | 4-methoxy | 3-methylthiophenyl |
| 52 | 3-chloro | 4-methoxy | 3-nitrophenyl |
| 70 | 4-cyano | 3-chloro | 3-methyl |
| 87 | 1-imidazolyl | H | 3-methylphenyl |
| 90 | 3-hydroxymethyl | 4-methoxy | 3-methylphenyl |
| 103 | 3-(t-butoxycarbamoyl methyl) | H | 3-(t-butoxycarbamoyl methyl)phenyl |

The compounds of Table II correspond to compounds of formula (II) wherein one of said B components is phenyl with two substituents, $Q^1$ and $Q^2$. In accordance with formula (II):

$Q^1$ is selected from $R^1$, $R^2$, $R^4$ or $R^5$; and $Q^2$ is selected from $R^1$ or $R^4$.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

As used herein, the compounds of this invention, including the compounds of formulae I–V, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae I–V.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $N-(C_{1-4}\text{ alkyl})_4^+$ salts. This invention also envisions the quaternization of any basic nitrogen-containing groups of the compounds disclosed herein. Water or oil-soluble or dispersible products may be obtained by such quaternization.

The compounds of this invention may be synthesized using conventional techniques. Advantageously, these compounds are conveniently synthesized from readily available starting materials.

In general, compounds of formula (I) are conveniently obtained via methods illustrated in General Synthetic Schemes 1–3.

In General Synthetic Scheme 1 (see below), an X-substituted aniline is reacted with a Y-substituted phenyl-isocyanate under standard conditions to give the desired urea. In this process, X and Y may be one or more independent substituents (or their suitably protected variants) as exemplified by the ring substituents listed for compounds of formulae I–V above, at any position on the aromatic ring.

General Synthetic Scheme 1:

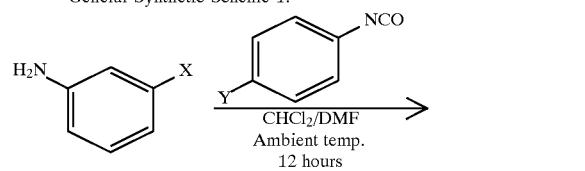

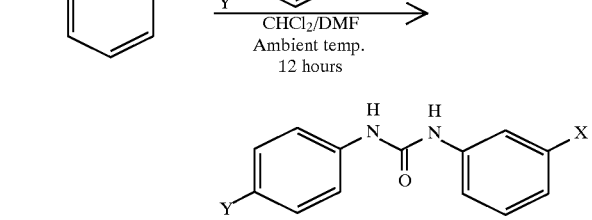

General Synthetic Scheme 2:

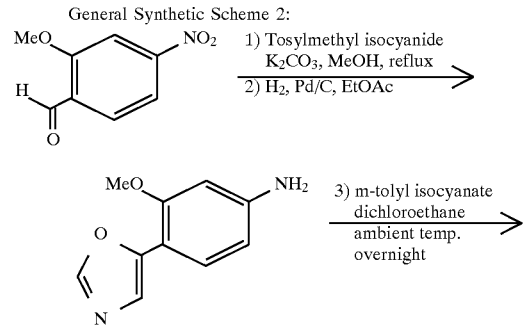

General Synthetic Scheme 3:

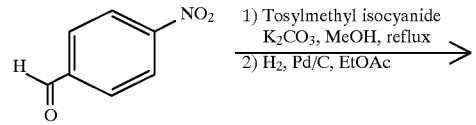

-continued

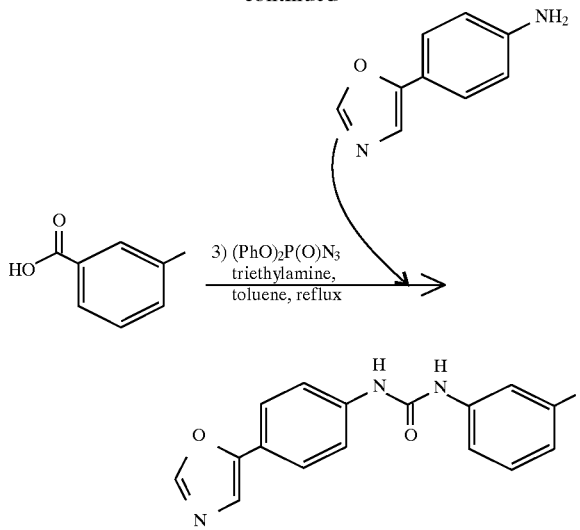

In General Synthetic Scheme 2 (see above), a substituted benzaldehyde (here, 2-methoxy-4-nitro-substituted) is treated sequentially with tosylmethylisocyanide, to give the resulting isoxazole, then reduced by catalytic hydrogenation to give the desired aniline. Reaction of this aniline with an isocyanate (here, m-tolylisocyanate) under standard conditions gives the desired urea.

An alternate synthetic route is illustrated in General Synthetic Scheme 3 (see above). A substituted benzaldehyde (here 4-nitro substituted) is converted to the corresponding isoxazolyl aniline as shown in General Synthetic Scheme 2. This aniline is treated with a substituted benzoic acid (here, 3-methyl-substituted) and a carboxylic acid activating agent, such as diphenylphosphoryl azide, under standard reaction conditions, to give the desired urea.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for IMPDH. Accordingly, these compounds are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). [See C. Montero et al., *Clinica Chimica Acta*, 238, pp. 169–178 (1995)].

Pharmaceutical compositions of this invention comprise a compound of formulae (I) or (II) or a pharmaceutically acceptable salt thereof; an additional agent selected from an immunosuppressant, an anti-cancer agent, an anti-viral agent, or an anti-vascular hyperproliferation compound; and any pharmaceutically acceptable carrier, adjuvant or vehicle. Alternate compositions of this invention comprise a compound of formulae (III)–(V) or a pharmaceutically acceptable salt thereof; and a pharmaceutically acceptable carrier, adjuvant or vehicle. Such composition may optionally comprise an additional agent selected from an immunosuppressant, an anti-cancer agent, an anti-viral agent, or an anti-vascular hyperproliferation compound.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of formulae I–V.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxy-ethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the IMPDH inhibitory compounds described herein are useful in a monotherapy for the prevention and treatment of IMPDH mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of an IMPDH inhibitor of formulae (I)–(V) and one or more additional therapeutic or prophylactic agents, both the IMPDH inhibitor and the additional agent should be present at dosage levels of between about 10 to 100%, and more preferably between about 10 to 80% of the dosage normally administered in a monotherapy regimen.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG and mizoribine.

According to an alternate embodiment, the pharmaceutical compositions of this invention may additionally comprise an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines and thioxantheres.

According to another alternate embodiment, the pharmaceutical compositions of this invention may additionally comprise an anti-viral agent. Examples of anti-viral agents include, but are not limited to, Cytovene, Ganciclovir, trisodium phosphonoformate, Ribavirin, d4T, ddI, AZT, and acyclovir.

According to yet another alternate embodiment, the pharmaceutical compositions of this invention may additionally comprise an anti-vascular hyperproliferative agent. Examples of anti-vascular hyperproliferative agents include, but are not limited to, lovastatin, thromboxane A2, synthetase inhibitors, eicosapentanoic acid, ciprostene, trapidil, ACE inhibitors, low molecular weight heparin and 5-(3'-pyridinylmethyl)benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In an alternate embodiment, this invention provides methods of treating or preventing IMPDH mediated disease in a a mammal comprising the step of administrating to said mammal any of the pharmaceutical compositions and combinations described above. If the pharmaceutical composition only comprises the IMPDH inhibitor of this invention as the active component, such methods may additionally comprise the step of administering to said mammal an agent selected from an immunosuppressant, an anti-cancer agent, an anti-viral agent, or an anti-vascular hyperproliferation compound. Such additional agent may be administered to the mammal prior to, concurrently with, or following the administration of the IMPDH inhibitor composition.

In a preferred embodiment, these methods are useful in suppressing an immune response in a mammal. Such methods are useful in treating or preventing diseases, including, transplant rejection and autoimmune diseases, such as rheumatoid arthritis, multiple sclerosis, juvenile diabetes, asthma, and inflammatory bowel disease.

These methods comprise the step of administering to the mammal a composition comprising a compound of any of formulae I–V and a pharmaceutically acceptable adjuvant. In a preferred embodiment, this particular method comprises the additional step of administering to said mammal a composition comprising an additional immunosuppressant and a pharmaceutically acceptable adjuvant.

Alternatively, this method comprises the step of administering to said mammal a composition comprising a compound of formulae I–V; an additional immunosuppressive agent and a pharmaceutically acceptable adjuvant.

In an alternate preferred embodiment, these methods are useful for inhibiting viral replication in a mammal. Such methods are useful in treating or preventing, for example, retroviral diseases, such as HTLV-1 and HTLV-2, HIV-1 and HIV-2, and Herpes viruses, such as Epstein-Barr, cytomegaloviruses and Herpes Simplex, Types 1 and 2. [See, U.S. Pat. No. 5,380,879].

These methods comprise the step of administering to the mammal a composition comprising a compound of any of formulae I–V, and a pharmaceutically acceptable adjuvant. In a preferred embodiment, this particular method comprises the additional step of administering to said mammal a composition comprising an additional anti-viral agent and a pharmaceutically acceptable adjuvant.

Alternatively, this method comprises the step of administering to said mammal a composition comprising a compound of formulae I–V; an additional anti-viral agent and a pharmaceutically acceptable adjuvant.

In another alternate preferred embodiment, these methods are useful for inhibiting vascular cellular hyperproliferation in a mammal. Such methods are useful in treating or preventing diseases, including, restenosis, and other hyperproliferative vascular disease.

These methods comprise the step of administering to the mammal a composition comprising a compound of any of formulae I–V, and a pharmaceutically acceptable adjuvant. In a preferred embodiment, this particular method comprises the additional step of administering to said mammal a composition comprising an additional anti-vascular hyperproliferative agent and a pharmaceutically acceptable adjuvant.

Alternatively, this method comprises the step of administering to said mammal a composition comprising a compound of formulae I–V; an additional anti-vascular hyperproliferative agent and a pharmaceutically acceptable adjuvant.

In another alternate preferred embodiment, these methods are useful for inhibiting tumors and cancer in a mammal. Such methods are useful in treating or preventing diseases, including, tumors and malignancies, such as lymphoma, leukemia and other forms of cancer.

These methods comprise the step of administering to the mammal a composition comprising a compound of any of formulae I–V, and a pharmaceutically acceptable adjuvant. In a preferred embodiment, this particular method comprises the additional step of administering to said mammal a composition comprising an additional anti-tumor or anti-cancer agent and a pharmaceutically acceptable adjuvant.

Alternatively, this method comprises the step of administering to said mammal a composition comprising a compound of formulae I–V; an additional anti-tumor or anti-cancer agent and a pharmaceutically acceptable adjuvant.

In order that this invention be more fully understood, the following examples are set forth. These examples are for the purpose of illustration only and are not to be construed as limiting the scope of the invention in any way.

General Materials and Methods

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Analytical HPLC was carried out using a Rainin Mycrosorb-MV, $5\mu$ Cyano reverse phase column, 3.9 mm×150 mm, with a flow rate of 1.0 mL/minute and a solvent gradient of 5–100% acetonitrile (0.1% TFA) in water (0.1% TFA). HPLC retention times were recorded in minutes. NMR spectral data was acquired using a Bruker AMX500 in the indicated solvent.

The IMP dehydrogenase HPLC assay follows our standard conditions for the enzymatic production of XMP and NADH from IMP and NAD, but utilizes high pressure liquid chromatography on a C18 column with ion pairing reagents to separate all four components. The extent of reaction is then determined from the resulting product peak areas. This assay is particularly useful for determining the inhibition profiles of compounds which have significant absorbance in the UV-visible region between 290 and 340 nM.

The reaction mixture typically contains 0.1M KPi; pH 8.0, 0.1M KCl, 0.5 mM EDTA, 2 mM DTT, and 0.2 mM each of IMP and NAD. This solution is incubated at 37° C. for 10 minutes. The reaction is started by the addition of enzyme to a final concentration of 20 to 100 nM, and is allowed to proceed for 10 minutes. After the allotted time, the reaction is quenched by the addition of mycophenolic acid to a final concentration of 0.01 mM.

The extent of conversion is monitored by HPLC using a Rainin Microsorb ODS column C18–200 of dimensions 4.6×10 mm and a solvent system containing tetrabutylammonium sulfate (5 mM) in 0.1M KPi pH 6.0 with a 0–30% methanol gradient over 15 minutes. A similar solvent system has been used previously for the purification of halo-IMP derivatives. [L. C. Antionio and J. C. Wu, *Biochemistry*, 33, 1753–1759 (1994).] A UV-monitor set at 254 nM is used to detect the four components, and the product peaks are integrated to determine the extent of conversion of the substrates.

For the analysis of inhibitors, the compound in question is dissolved in DMSO to a final concentration of 20 mM and added to the initial assay mixture at the desired concentration in a volume of 2–5% (v/v). The reaction is started by the addition of enzyme and after 10 minutes is quenched as above. After HPLC analysis, the product areas are used to determine the extent of conversion relative to a control assay containing only DMSO and no test compound. IC50 or Ki values are determined from non linear least squares fitting of conversion vs concentration curves to the tight-binding equations of Henderson. [P. J. F. Henderson, *Biochem. J.*, 127, 321 (1972).]

We have measured the inhibition constants of each compound against IMPDH using an adaptation of the method first reported by Magasanik. [B. Magasanik, H. S. Moyed, and L. B. Gehring *J. Biol. Chem.*, 226, p.339 (1957)].

Insofar as compounds of formulae I–V are able to inhibit IMPDH, they are of evident clinical utility for the treatment of IMPDH mediated disease. These tests are predictive of the compounds ability to inhibit IMPDH in vivo.

Experimental Section

Synthesis of Representative Examples:

EXAMPLE 1

Synthesis of Compound 1

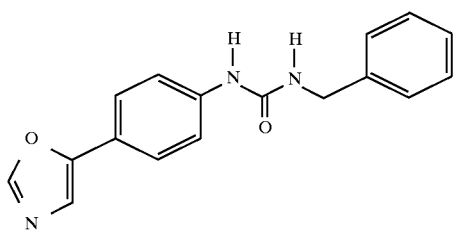

To a solution of 25 mg (156 μmole) 4-(5-oxazolyl)-aniline in 250 μL $CH_2Cl_2$ was added 50 μL (400 μmole) of benzyl isocyanate at ambient temperature. After stirring overnight, 1 was isolated in pure form by filtration with a 3:1 hexanes/$CH_2Cl_2$ rinse in a yield of 21 mg (46%). $^1$H NMR (500 MHz, $CDCl_3$) δ 7.86(s), 7.55(d), 7.38(d), 7.22–7.35(m), 6.39(s), 5.0(br s), 4.43(s). $R_f$ 0.30 (5% MeOH/$CH_2Cl_2$).

EXAMPLE 2

Synthesis of Compound 43

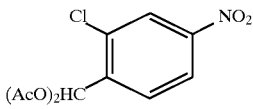

To a solution of glacial acetic acid (46 mL), acetic anhydride (46 mL, 485 mmole) and 2-chloro-4-nitrotoluene (5 g, 29.1 mmole) at 0° C. was added conc. $H_2SO_4$ (6.9 mL) in a dropwise fashion. Upon complete addition, $CrO_3$ (8.08 g, 80.8 mmole) was added portion-wise over 60 mins. Following an additional 15 mins of stirring at 0° C., the reaction mixture was poured over ice and the resulting precipitate was isolated by filtration, rinsing with cold $H_2O$. Purification by flash chromatography, eluting with a gradient of 15–50% EtOAc in hexanes, provided 2.02 g (24%, 40% based on recovered starting material) B1 as a white solid. The $^1$H NMR was consistent with that of the desired structure.

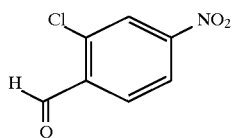

Compound B1 was dissolved in 1:1 ethanol/water (20 mL), treated with conc. $H_2SO_4$ (2 mL) and refluxed for 1 hour. Upon cooling to ambient temperature, the reaction was extracted 3x's with diethyl ether. The ethereal solution was washed twice with water, dried over $Na_2SO_4$ and concentrated in vacuo to yield a yellow solid. Purified product was obtained through two recrystallizations from hot $Et_2O$/hexanes, yielding 620 mg (47.6%) B2 as a lightly yellowed crystalline solid. The $^1$H NMR was consistent with that of the desired structure.

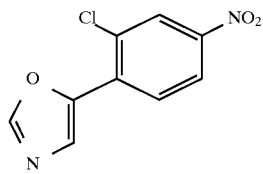

A mixture of B2 (200 mg, 1.2 mmol), tosylmethyl isocyanide (236 mg, 1.2 mmol), and powdered $K_2CO_3$ (172 mg, 1.2 mmole) in methanol (13 mL) was heated at reflux for 90 minutes and then stirred overnight at ambient temperature. Upon concentration to dryness, the mixture was partitioned between $CH_2Cl_2$ and water. The organics were separated, washed with 0.5N HCl, water and brine and then dried over $Na_2SO_4$. The solvent was removed in vacuo to provide a crude yellow solid. Purified product B3 was obtained through flash chromatography, eluting with a gradient of 0–2.5% $CH_3OH$ in $CH_2Cl_2$, and recrystallization ($CH_2Cl_2$/hexanes) in a yield of 3.3 g (68%) as a light yellow crystalline solid. The $^1$H NMR was consistent with that of the desired structure.

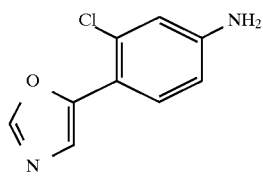

A solution of B3 (150 mg, 0.67 mmole) in ethanol (7.5 mL) was treated with $SnCl_2 \cdot 2H_2O$ (excess; ca. 5 equivalents) and heated at reflux for 30 minutes. The mixture was cooled to ambient temperature, diluted with diethyl ether and partitioned with 2N NaOH. The organics were separated, washed with water and brine, dried over $Na_2SO_4$ and concentrated in vacuo. Purified product B4 was obtained through flash chromatography, eluting with a gradient of 0–0.5% $CH_3OH$ in $CH_2Cl_2$, in a yield of 54 mg (41.5%) as a light yellow oil. The $^1$H NMR was consistent with that of the desired structure.

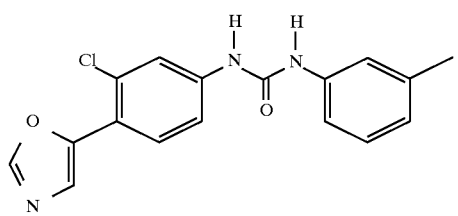

To a solution of 20 mg (103 μmole) B4 in 1 mL $CH_2Cl_2$ was added 20 μL m-tolylisocyanate at ambient temperature. After stirring overnight, 43 was isolated in pure form by filtration with an EtOAc/hexanes rinse in a yield of 25 mg (74%). $^1$H NMR (500 MHz, $d_6$-DMSO) δ 9.06 (s), 8.73 (s), 8.50 (s), 7.89 (s), 7.73 (d), 7.67 (s), 7.42 (d), 7.31 (s), 7.23 (d), 7.18 (t), 6.82 (d), 2.27 (s). $R_f$ 0.28 (5% MeOH/$CH_2Cl_2$).

EXAMPLE 3

Synthesis of Compound 56

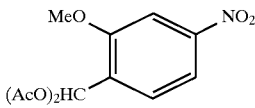

C1 (8.14 g, 51%) was prepared from 2-methyl-5-nitroanisole (10.0 g, 60 mmole) in a fashion directly analogous to the preparation of B1 as described above. The $^1$H NMR was consistent with that of the desired structure.

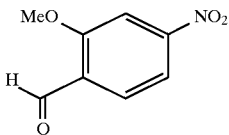

A stirred suspension of C1 (81.94 g, 307 mmole) in dioxane (100 mL) was treated with concentrated HCl (20 mL) and heated at reflux overnight. Upon cooling to ambient temperature, the product C2 precipitated as a light yellow crystalline solid in a yield of 40.65 g (73.1%). The filtrate was concentrated to a volume of ca. 80 mL and a second crop of product crystals was driven from solution by the addition of hexanes, yielding 8.91 g (16.0%). Both batches were identical by $^1$H NMR and TLC analysis and were consistent with that of the desired material. The total yield of C2 was 49.56 g (89.1%).

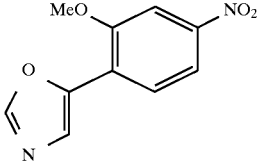

A solution of C2 (456 mg, 2.51 mmole), tosylmethyl isocyanide (490 mg, 2.51 mmole) and $K_2CO_3$ (347 mg, 251 mmole) were dissolved in methanol and heated to reflux for 1.5 hours. The product mixture was then concentrated in vacuo, redissolved in $CH_2Cl_2$, washed with water and brine, dried over $Na_2SO_4$ and again concentrated in vacuo. Purified product C3 was obtained through recrystallization ($Et_2O$/hexanes) to yield 375 mg (68%). The $^1$H NMR was consistent with that of the desired structure.

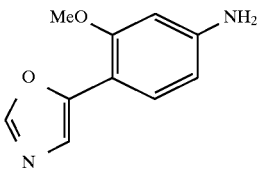

A solution of C3 (4.214 g, 19.1 mmole) in EtOAc (150 mL) was treated with 10%Pd/C (1.05 g, 25 wt.% of C3) and subjected to 40 psi $H_2$ (g) (Parr Hydrogenation Apparatus) overnight. The reaction mixture was filtered and concentrated in vacuo. Pure product C4 was obtained through flash chromatography, eluting with a gradient of 30–40% EtOAc/hexanes, in a yield of 3.4 g (93%). The $^1$H NMR was consistent with that of the desired structure.

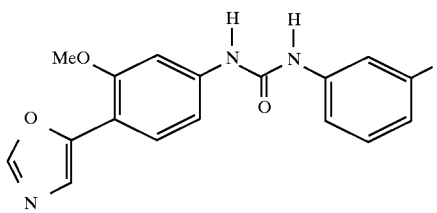

To a solution of C4 (25 mg, 0.131 mmole) in $CH_2Cl_2$ (1 mL) was added toll isocyanate (25 μL, 0.197 mmole) at ambient temperature. After stirring overnight, 56 was isolated in pure form by filtration with a $CH_2Cl_2$ rinse in a yield of 42 mg (74%). $^1$H NMR (500 MHz, $d_6$-DMSO) δ 8.87 (s), 8.64 (s), 8.37 (s), 7.60 (d), 7.46 (d), 7.42 (s), 7.33 (s), 7.23 (d), 7.16–7.19 (t), 7.05 (dd), 6.80 (d), 3.92 (s), 2.28 (s). $R_f$ 0.46 (5% MeOH/$CH_2Cl_2$).

EXAMPLE 4

Synthesis of Compound 59

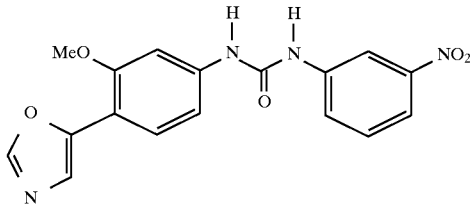

To a solution of C4 (75 mg, 0.394 mmole) in dichloroethane (5 mL) was added 3-nitrophenyl isocyanate (97 mg, 0.59 mmole) at ambient temperature. After stirring overnight, D1 was isolated in pure form by filtration with a $CH_2Cl_2$ rinse in a yield of 110.3 mg (79%). The $^1$H NMR was consistent with that of the desired structure.

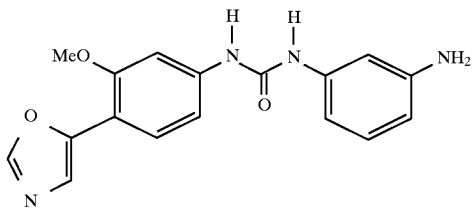

To a stirred suspension of D1 (95 mg, 0.268 mmole) in EtOH (20 mL) was added $SnCl_2 \cdot 2H_2O$ (302 mg, 1.34 mmole). The reaction mixture was brought to reflux, at which time dissolution occurred, for 1.5 hours. The solution was cooled to ambient temperature, diluted with EtOAc, washed with 2N NaOH and brine, dried ($Na_2SO_4$) and concentrated in vacuo. Pure product 59 was obtained through flash chromatography (eluting with a gradient of 2.5–5% MeOH in $CH_2Cl_2$), followed by selective crystallization of the desired material from slightly impure fractions in a yield of 15.7 mg (18%). $^1$H NMR (500 MHz, $d_6$-DMSO) δ 8.83 (s), 8.44 (s), 8.35 (s), 7.59 (d), 7.48 (d), 7.40 (s), 6.97–7.04 (dd), 6.86–6.92 (t), 6.83 (d), 6.54 (dd), 6.20 (dd), 5.05 (br s), 3.92 (s). $R_f$ 0.20 (5% MeOH/$CH_2Cl_2$).

EXAMPLE 5

Synthesis of Compound 113

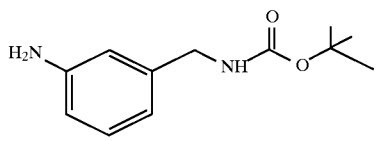
E1

A solution of 3-aminobenzylamine (826 mg, 6.87 mmole) and triethylamine (2.39 mL, 17.18 mmole) was treated with di-t-butyldicarbonate (1.50 g, 6.87 mmole) and the mixture was stirred at ambient temperature for 2 hours. The reaction was then diluted with $CH_2Cl_2$, washed with $NaHCO_3$(aq), water and brine, dried ($Na_2SO_4$) and concentrated in vacuo. Pure E1 was obtained by flash chromatography, eluting with 25% EtOAc in hexanes in a yield of 200 mg (46%). The $^1H$ NMR was consistent with that of the desired structure.

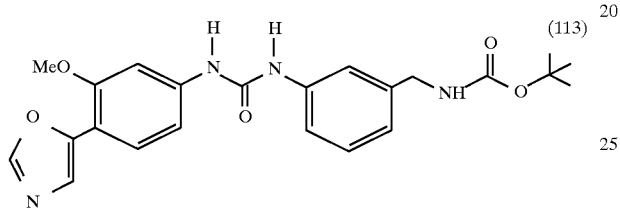
(113)

A solution of C4 (150 mg, 0.789 mmole) and 1,1-dicarbonylimidiazole (160 mg, 0.986 mmole) were combined in THF (5 mL) and stirred for 6 hours at ambient temperature. The precipitation of imidazole was noted. To this was then added E1 (351 mg, 1.58 mmole) and N,N-dimethylaminopyridine (97 mg, 0.789 mmole) and the mixture was refluxed overnight, resulting in a homogenous solution. Upon cooling to ambient temperature, the reaction was diluted with EtOAc (20 mL), washed with $KHSO_4$(aq), water, and brine, dried ($MgSO_4$) and concentrated. Pure 113 was obtained through flash chromatography, eluting with a gradient of 20–30–35% acetone in hexanes in a yield of 164 mg (47%). $^1H$ NMR (500 MHz, $d_6$-DMSO) δ 8.90 (s), 8.75 (s), 8.38 (s), 7.60 (d), 7.51 (s), 7.3–7.46 (m), 7.21–7.27 (t), 7.05 (dd), 6.87 (d), 4.12 (d), 3.93 (s), 1.44 (s). $R_f$ 0.21 (5% MeOH/$CH_2Cl_2$).

EXAMPLE 6

Synthesis of Compound 70

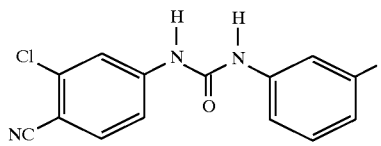
(70)

A solution of 3-chloro-4-cyanoaniline (500 mg, 7.76 mmole) and m-tolylisocyanate (1.0 mL, 3.17 mmole) in $CH_2Cl_2$ (3 mL) was stirred overnight at ambient temperature. The reaction mixture was concentrated and pure 70 was obtained through MPLC, eluting with 1% MeOH in $CH_2Cl_2$, in a yield of 285 mg (31%). $^1H$ NMR (500 MHz, $d_6$-DMSO) δ 9.36 (s), 8.88 (s), 7.94 (s), 7.83 (d), 7.44 (d), 7.30 (s), 7.24 (d), 7.15–7.20 (t), 6.82 (d), 2.29 (s). $R_f$ 0.36 (5% MeOH/$CH_2Cl_2$).

EXAMPLE 7

Synthesis of Compound 108

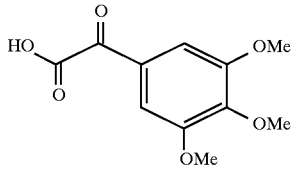
G1

To a solution of 3,4,5-trimethoxyacetophenone (9.2 g, 43.4 mmol) in pyridine (35 mL) was added selenium dioxide (6.3 g, 56.7 mmol) and the resulting solution was heated at reflux overnight. The reaction mixture was cooled to ambient temperature, filtered through celite and concentrated to yield a dark brown oil which was dissolved into ethyl acetate and washed with 1.0N HCl and then with saturated $NaHCO_3$. The basic aqueous layer was diluted with ether and acidified with concentrated HCl. The layers were separated and the organic phase was washed with brine and then dried ($Na_2SO_4$) to give 8.4 g of a dark yellow solid.

Recrystallization of this material from ethyl acetate-hexane then gave G1 (6.8 g) as a pale yellow solid. The $^1H$ NMR was consistent with that of the desired structure.

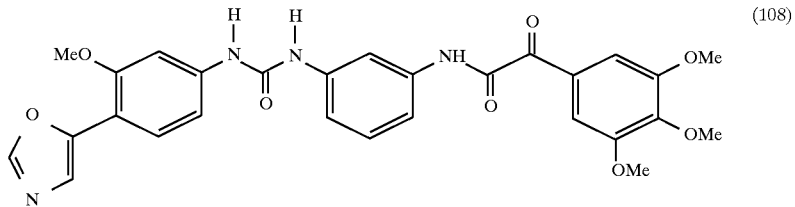
(108)

A mixture of 59 (64 mg, 0.20 mmole), G1 (300 mg, 1.20 mmole) and EDC (300 mg, 1.6 mmole) in THF (5 mL) was stirred overnight at ambient temperature. The reaction was diluted with EtOAc (150 mL), washed with water, dried ($MgSO_4$) and concentrated in vacuo. Pure 108 was obtained through MPLC, eluting with a gradient system of 0–1%MeOH in $CH_2Cl_2$, in a yield of 37.4 mg (35%). $^1H$ NMR (500 MHz, $d_6$-DMSO) δ 9.83 (s), 8.23 (s), 8.18 (s), 7.65 (s), 7.61 (s), 7.35 (d), 7.33 (s), 7.29 (s), 7.27 (s), 7.11 (s), 7.06–7.10 (t), 6.94–6.99 (t), 6.52 (d)3.68 (s), 3.63 (s), 3.61(s). $R_f$ 0.26 (5% MeOH/$CH_2Cl_2$).

EXAMPLE 8

Synthesis of Compound 115

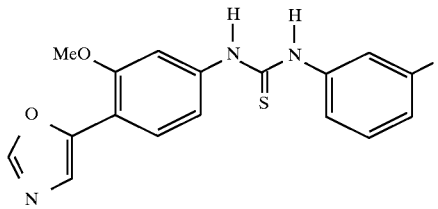

(115)

A solution of 59 (300 mg, 1.58 mmole) and m-toll isothiocyanate (2.0 mL, 14.7 mmole) in CH$_2$Cl$_2$ (5 mL) was stirred at ambient temperature overnight. To drive the reaction to completion, additional m-toll isothiocyanate (1.0 mL, 7.4 mmole) was added and the mixture was heated to reflux for 3 hours. The reaction was concentrated in vacuo and 115 was obtained in pure form through MPLC, eluting with 0–5% EtOAc in CH$_2$Cl$_2$, in a yield of 210 mg (39%). H NMR (500 MHz, d$_6$-DMSO) δ 7.90 (s), 7.89 (s), 7.82 (s), 7.75 (d), 7.64 (s) 7.44 (s), 7.32–7.37 (t), 7.27 (s), 7.13–7.21 (m), 6.91 (dd), 3.98 (s), 2.40 (s). R$_f$ 0.36 (5% MeOH/CH$_2$Cl$_2$).

EXAMPLE 9

Synthesis of Compound 97

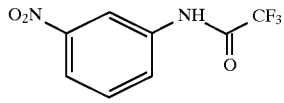

I1

A solution of nitroaniline (1.0 g, 7.13 mmole) in CH$_2$Cl$_2$ (25 mL) was treated with pyridine (2.9 mL, 36 mmole) and trifluoroacetic anhydride (5 mL, 36 mmole) and stirred at ambient temperature for 3 hours. The reaction was diluted further with CH$_2$Cl$_2$, washed with 1N HCl and brine, dried (MgSO$_4$) and concentrated in vacuo to yield I1 (1.61 g, 95%) as a white solid. The $^1$H NMR was consistent with that of the desired structure.

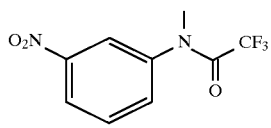

I2

To a slurry of NaH (60% oil dispersion; 34 mg, 1.42 mmole) in THF (10mL) at 0° C. was added a solution of I1 (200 mg, 0.8 mmole) in THF (10 mL) and the mixture stirred for 1 hour. To this was added methyl iodide (100 µL, 1.7 mmole) and the mixture was stirred overnight at ambient temperature. The reaction was poured into water and extracted with EtOAc. The organics were separated, dried (MgSO$_4$) and concentrated in vacuo. Pure I2 was obtained through flash chromatography, eluting with 5% EtOAc in hexanes, in a yield of 163 mg (66%) as a yellow solid. The $^1$H NMR was consistent with that of the desired structure.

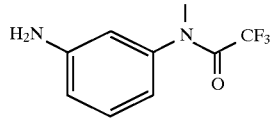

I3

A solution of I2 (163 mg, 0.66 mmole) in ethanol (5 mL) was treated with Pd/C (20 mg) and subjected to H$_2$ (1 atm.) for 3 hours. The reaction was filtered and concentrated in vacuo to yield I3 (120 mg, 84%) as a waxy solid. The $^1$H NMR was consistent with that of the desired structure.

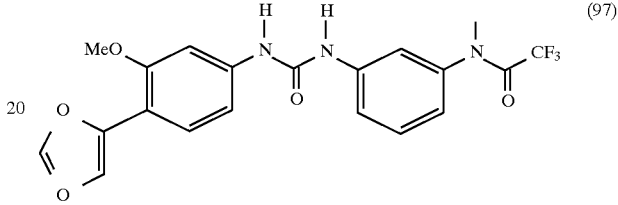

(97)

To a solution of triphosgene (31 mg, 0.104 mmole) in dichloroethane (1 mL) was added in a dropwise fashion a solution of B4 (50 mg, 0.260 mmole) and diisopropylethylamine (67 mg, 518 mmole) in dichloroethane (5 mL). The reaction mixture was stirred for an additional 1 hour at ambient temperature, treated with I3 (50 mg, 0.230 mmole) and stirred overnight. The entire reaction mixture was subjected to flash chromatography, eluting with 1% MeOH in CH$_2$Cl$_2$, to provide pure 97 in a yield of 8 mg (7%). $^1$H NMR (500 MHz, d$_6$-DMSO) δ 9.20 (s), 8.98 (s), 8.39 (s), 7.67 (s), 7.63 (d), 7.48 (s), 7.38–7.45 (m), 7.04–7.10 (t), 3.95 (s), 3.31 (s). R$_f$ 0.37 (5% MeOH/CH$_2$Cl$_2$).

EXAMPLE 10

Synthesis of Compound 111

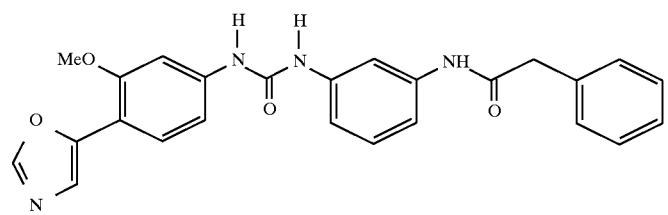

(111)

A solution of 59 (50 mg, 0.154 mmole) and triethylamine (31 mg, 0.308 mmole) in DMF (0.5 mL) was treated in a dropwise fashion with phenylacetyl chloride (25 mg, 0.169 mmole) and the reaction stirred overnight at ambient temperature. The mixture was diluted with CH$_2$Cl$_2$, washed with NaHCO$_3$(aq) and water, dried over MgSO$_4$ and concentrated in vacuo. Pure 111 was isolated by flash chromatography, eluting with 2% MeOH in CH$_2$Cl$_2$, in a yield of 42 mg (62%). $^1$H NMR (500 MHz, d$_6$-DMSO) δ 10.20(s), 8.90 (s), 8.79 (s), 8.39 (s), 7.88 (s), 7.63 (d), 7.53 (d), 7.44 (s), 7.25–7.40 (m), 7.22 (t), 7.14 (d), 7.05 (dd), 3.96 (s), 3.66 (s) R$_f$ 0.31 (5% MeOH/CH$_2$Cl$_2$).

EXAMPLE 11

Synthesis of Compound 102

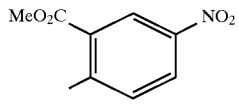 K1

A solution of 2-methyl-5-nitrobenzoic acid (15 g, 82.8 mmole) in DMF (75 mL) was treated with methyl iodide (6.7 mL, 107.64 mmole) followed by powdered $K_2CO_3$ (17.2 g, 124.2 mmole) (extreme exotherm) and the suspension stirred at ambient temperature overnight. The reaction mixture was partitioned between EtOAc and water, the organics separated and washed with water and brine, dried ($Na_2SO_4$) and concentrated in vacuo to yield K1 (15.86 g, 98%) in pure form as an off-white solid. The $^1$H NMR was consistent with that of the desired structure.

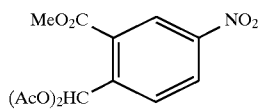 K2

K2 (4.09 g, 16.2%) was prepared from K1 (15.86 g, 81.3 mmole) in a fashion analogous to the preparation of B1 as described above. The $^1$H NMR was consistent with that of the desired structure.

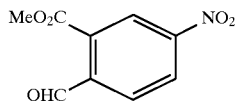 K3

A solution of K2 (2.5 g, 8.03 mmole) in dioxane (10 mL) was treated with conc. HCl (0.5 mL) and the mixture was heated to reflux for 2 hours. Additional conc. HCl (0.5 mL) was added and the reaction refluxed for 3 hours longer. The mixture was diluted with EtOAc, washed with water and brine, dried ($Na_2SO_4$) and concentrated in vacuo. Pure K3 was obtained through flash chromatography, eluting with a gradient of 20–30–50% $Et_2O$ in hexanes, in a yield of 1.14 g (68%). Also isolated was 215 mg (11.8%) of the hydrated aldehyde. The $^1$H NMRs were consistent with that of the desired structures.

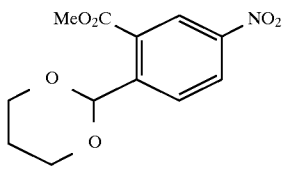 K4

A solution of K3 (300 mg, 1.43 mmole) in benzene (5 mL) was treated with 1,3-propane diol (114 μL, 1.573 mmole) and p-TsOH•$H_2O$ (27 mg, 0.14 mmole) and the mixture was refluxed with Dean-Stark removal of water for 4.5 hours. The reaction was cooled to ambient temperature, partitioned between EtOAc and dilute $NaHCO_3$, the organics separated, washed with brine, dried ($Na_2SO_4$) and concentrated in vacuo. Pure K4 was obtained through flash chromatography, eluting with a gradient of 20–25% $Et_2O$ in hexanes, in a yield of 324 mg (84.5%) as an off-white crystalline solid. The $^1$H NMR was consistent with that of the desired structure.

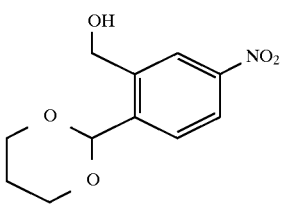 K5

A solution of K4 (289 mg, 1.08 mmole) in THF (5 mL) at 0° C. was treated dropwise with a solution of DIBAL (1.0M in $CH_2Cl_2$; 2.7 mL, 2.7 mmole) and stirred for 40 minutes. The reaction was quenched by addition of saturated Rochelle's salt solution (10mL), diluted with EtOAc and stirred for 30 minutes. The organics were collected, washed with brine, dried ($Na_2SO_4$) and concentrated in vacuo to give 250 mg (97%) of K5 as a white crystalline solid. The $^1$H NMR was consistent with that of the desired structure.

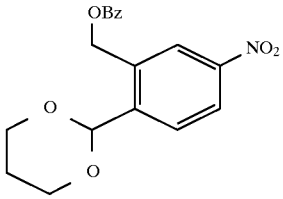 K6

A solution of K5 (250 mg, 1.05 mmole) in $CH_2Cl_2$ (4 mL) at 0° C. was treated with pyridine (110 μL, 1.37 mmole), benzoyl chloride (146 μL, 1.26 mmole) and 4-DMAP (catalytic), and stirred at ambient temperature overnight. The reaction mixture was diluted with $CH_2Cl_2$, washed with 0.5N HCl, water and brine, dried ($Na_2SO_4$) and concentrated in vacuo. Pure K6 was obtained through flash chromatography, eluting with 10% EtOAc in hexanes, in a yield of 340 mg (99%) as a white solid. The $^1$H NMR was consistent with that of the desired structure.

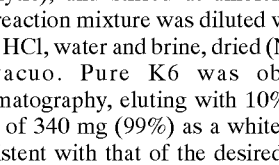 K7

A solution of K6 (326 mg, 0.99 mmole) in dioxane (7 mL) was treated with 2.0N HCl (5 mL) and the mixture heated at 80° C. overnight. The reaction mixture was diluted with EtOAc and washed with saturated $NaHCO_3$(aq), water and brine, dried ($Na_2SO_4$) and concentrated in vacuo. Pure K7 was obtained through flash chromatography, eluting with 30% $Et_2O$ in hexanes, in a yield of 208 mg (77.5%) as a white solid. The $^1$H NMR was consistent with that of the desired structure.

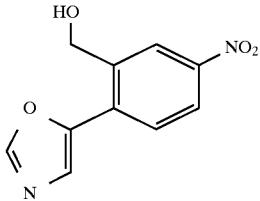 K8

A solution of K7 (208 mg, 0.729 mmole) in MeOH (6 mL) was treated with $K_2CO_3$ (101 mg, 0.76 mmole) and TosMIC (149 mg, 0.765 mmole) and the solution heated at 60° C. for one hour. The reaction was concentrated in vacuo, redissolved in $CH_2Cl_2$ and washed with 1.0N NaOH (diluted with saturated NaHCO₃). The aqueous portion was back-extracted with CH₂Cl₂, the organics combined and washed with water and brine, dried (Na₂SO₄) and concentrated in vacuo. Pure K8 was obtained through flash chromatography, eluting with a gradient of 10–50% acetone in hexanes, in a yield of 70 mg (44%). The ¹H NMR was consistent with that of the desired structure.

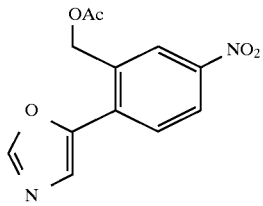

K9

A solution of K8 (70 mg, 0.318) in acetic anhydride (1.5 mL) and pyridine (1.0 mL) was treated with 4-DMAP (catalytic) and stirred at ambient temperature for 3 hours. The mixture was diluted with CH₂Cl₂, washed with 1.0N HCl, water and brine, dried (Na₂SO₄) and concentrated in vacuo to provide K9 in a yield of 82 mg (98%) as a pale yellow solid. The ¹H NMR was consistent with that of the desired structure.

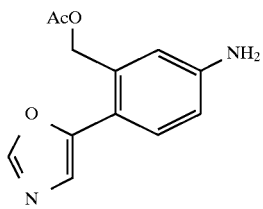

K10

A solution of K9 (80 mg, 0.305 mmole) in dry EtOH (4 mL) was treated with SnCl₂·2H₂O (241 mg, 1.07 mmole) and the mixture heated at 60° C. for 50 minutes. The reaction was diluted with EtOAc, washed with saturated NaHCO₃, water and brine, dried (Na₂SO₄) and concentrated in vacuo. Pure K10 was obtained through flash chromatography, eluting with a gradient of 20–30% acetone in hexanes, in a yield of 52 mg (73.4%) as a pale yellow oil. The ¹H NMR was consistent with that of the desired structure.

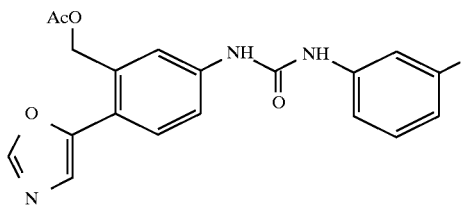

K11

A solution of K10 (52 mg, 0.224 mmole) in dichloroethane (2 mL) was treated with m-toll isocyanate (43 μL, 0.336 mmole) and stirred overnight at ambient temperature. The mixture was diluted with CH₂Cl₂:hexanes (2:1), filtered and rinsed with the same solvent system to provide K11 (67 mg, 82%) as a white solid. The ¹H NMR was consistent with that of the desired structure.

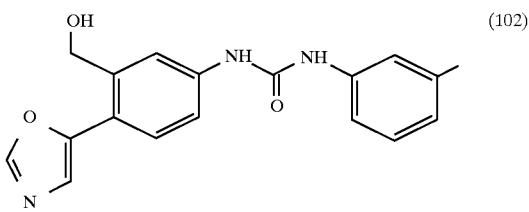

(102)

A solution of K11 (33 mg, 0.09 mmole) in MeOH (2 mL) was treated with 1.0N NaOH (135 μL, 0.135 mmole) and stirred at ambient temperature for 1.5 hours. The reaction was neutralized by addition of 1.0N HCl (135 μL) and concentrated in vacuo. The white solid was rinsed with water and CH₂Cl₂:hexanes (2:1) and dried in vacuo to provide 102 (20 mg, 68%) as a white solid. 1H NMR (500 MHz, d₆-DMSO) δ 9.29 (s), 9.00 (s), 8.42 (s), 7.69 (s), 7.55 (m), 7.37 (s), 7.33 (s), 7.27 (d), 7.16 (t), 6.80 (d), 5.39 (t), 4.58 (s), 2.28 (s). R_f 0.13 (1:1 hexanes/acetone).

EXAMPLE 12

Synthesis of Compound 106

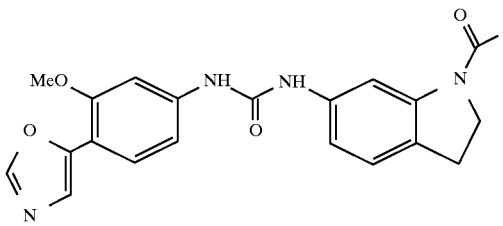

A solution of C4 (50 mg, 0.263 mmole) in THF (2 mL) was treated with CDI (53 mg, 0.330 mmole) and stirred at ambient temperature for 4 hours. To this was added 1-acetyl-6-aminoindole (93 mg, 0.526 mmole, Sigma Chemical Co.) and 4-DMAP (35 mg, 0.289 mmole) and the mixture refluxed overnight. Diluted with EtOAc (100 mL), washed with 5% KHSO₄₁ water and brine, dried (Na₂SO₄) and concentrated in vacuo. Redissolved in EtOAc and filtered to removed insoluble materials and reconcentrated in vacuo. Pure 106 was obtained through flash chromatography, eluting with a gradient of 50–60% acetone in hexanes, in a yield of 37 mg (36%) as a white solid. ¹H NMR (500 MHz, d₆-DMSO) δ 8.79 (s), 8.74 (s), 8.37 (s), 8.11 (s), 7.62 (d), 7.47 (s), 7.43 (s), 7.30 (d), 7.13 (d), 7.14 (d), 4.11 (t), 3.94 (s), 3.07 (t), 2.17 (s). R_f 0.14 (1:1 hexanes/acetone).

EXAMPLE 13

IMPDH Activity Inhibition Assay

We measured the inhibition constants of the compounds listed in Table III utilizing the following protocol:

IMP dehydrogenase activity was assayed following an adaptation of the method first reported by Magasanik. [Magasanik, B. Moyed, H. S. and Gehring L. B. (1957) *J. Biol. Chem.* 226, 339]. Enzyme activity was measured spectrophotometrically, by monitoring the increase in absorbance at 340 nm due to the formation of NADH (ε340 is 6220M⁻¹ cm⁻¹). The reaction mixture contained 0.1M Tris pH 8.0, 0.1M KCl, 3 MM EDTA, 2 mM DTT, 0.1M IMP and enzyme (IMPDH human type II) at a concentration of 15 to 50 nM. This solution is incubated at 37° C. for 10 minutes. The reaction is started by adding NAD to a final concentration of 0.1M and the initial rate is measured by following the linear increase in absorbance at 340 nm for 10 minutes. For reading in a standard spectrophotometer (path length 1 cm) the final volume in the cuvette is 1.0 ml. The assay has also been adapted to a 96 well microtiter plate format; in this case the concentrations of all the reagents remain the same and the final volume is decreased to 200 μl.

For the analysis of inhibitors, the compound in question is dissolved in DMSO to a final concentration of 20 mM and added to the initial assay mixture for preincubation with the enzyme at a final volume of 2–5% (v/v). The reaction is started by the addition of NAD, and the initial rates measured as above. $K_i$ determinations are made by measuring the initial velocities in the presence of varying amounts of inhibitor and fitting the data using the tight-binding equations of Henderson (Henderson, P. J. F. (1972) *Biochem. J.* 127, 321].

These results are shown in Table III. $K_i$ values are expressed in nM. The designation "ND" is used where a given compound was not tested.

TABLE III

| Cmpd # | $K_i$ | Cmpd # | $K_i$ | Cmpd # | $K_i$ |
|---|---|---|---|---|---|
| 1 | 10000 | 40 | 4800 | 78 | 300 |
| 2 | 3300 | 41 | 8000 | 79 | 100 |
| 3 | 1000 | 42 | 280 | 80 | 3500 |
| 4 | 15000 | 43 | 55 | 81 | 9000 |
| 5 | 7000 | 44 | 75 | 82 | 9000 |
| 6 | 3300 | 45 | 3500 | 83 | 120 |
| 7 | 960 | 46 | 430 | 84 | 300 |
| 8 | 1400 | 47 | 650 | 85 | 1000 |
| 9 | 5200 | 48 | 2500 | 86 | 1700 |
| 10 | 3500 | 49 | 6000 | 87 | 12000 |
| 11 | 6500 | 50 | 19500 | 88 | 4000 |
| 12 | 5000 | 51 | 12500 | 89 | 3300 |
| 13 | 4000 | 52 | 9500 | 90 | 10000 |
| 14 | 8000 | 53 | 7000 | 91 | 3500 |
| 15 | 1500 | 54 | 1700 | 92 | 4000 |
| 16 | 7400 | 55 | 20 | 93 | 40 |
| 17 | 510 | 56 | 70 | 94 | 750 |
| 18 | 1020 | 57 | 135 | 95 | 2000 |
| 19 | 6200 | 58 | 8000 | 96 | 220 |
| 20 | 1500 | 59 | 20 | 97 | 12 |
| 21 | 2700 | 60 | 65 | 98 | 150 |
| 22 | 1020 | 61 | 18000 | 99 | 35 |
| 23 | 4100 | 62 | 4000 | 100 | 180 |
| 24 | 520 | 63 | 1400 | 101 | 7000 |
| 25 | 1140 | 64 | 615 | 102 | 2500 |
| 26 | 8500 | 65 | 95 | 103 | 2000 |
| 27 | 5200 | 66 | 4500 | 104 | 4000 |
| 28 | 4600 | 67 | 3400 | 105 | 250 |
| 29 | 16000 | 68 | 1000 | 106 | 300 |
| 30 | 5100 | 69 | 250 | 107 | 17 |
| 31 | 13000 | 70 | 1200 | 108 | 115 |
| 32 | 18000 | 71 | 1800 | 109 | 700 |
| 33 | 12500 | 72 | 1400 | 110 | 150 |
| 34 | 4300 | 73 | 450 | 111 | 45 |
| 35 | 9000 | 74 | 300 | 112 | 85 |
| 36 | 9000 | 75 | 80 | 113 | 15 |
| 37 | 4500 | 76 | 3000 | 114 | 80 |
| 38 | 15000 | 77 | 65 | 115 | 625 |
| 39 | 12000 | | | | |

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments which have been presented by way of example.

We claim:
1. A compound of the formula:

wherein:
E is oxygen;
G and G' are independently selected from the group consisting of $R^6$ and $(CH_2)_n$—Y;
D is selected from the group consisting of C(O), C(S) and $S(O)_2$;
B is phenylene;
B' is phenyl;
wherein each of B and B' optionally comprises up to 3 substituents, wherein:
  the first of said substituents, if present, is selected from $R^1$, $R^2$, $R^4$ or $R^5$,
  the second of said substituents, if present, is selected from $R^1$ or $R^4$, and
  the third of said substituents, if present, is $R^1$;
  wherein:
    each $R^1$ is independently selected from 1,2-methylenedioxy, 1,2-ethylenedioxy, $R^6$ or $(CH_2)_n$—Y;
    wherein n is 0, 1 or 2; and
    Y is selected from halogen, CN, $NO_2$, $CF_3$, $OCF_3$, OH, $SR^6$, $S(O) R^6$, $SO_2R^6$, $NH_2$, $NHR^6$, $N(R^6)_2$, $NR^6R^8$, COOH, $COOR^6$ or $OR^6$;
    each $R^2$ is independently selected from $(C_1–C_4)$-straight or branched alkyl, or $(C_2–C_4)$-straight or branched alkenyl or alkynyl; and each $R^2$ optionally comprises up to 2 substituents, wherein:
      the first of said substituents, if present, is selected from $R^1$, $R^4$ and $R^5$, and
      the second of said substituents, if present, is $R^1$;
    each $R^4$ is independently selected from $OR^5$, $OC(O)R^6$, $OC(O)R^5$, $OC(O)OR^6$, $OC(O)OR^5$, $OC(O)N(R^6)_2$, $OP(O)(OR^6)_2$, $SR^6$, $SR^5$, $S(O)R^6$, $S(O)R^5$, $SO_2R^6$, $SO_2R^5$, $SO_2N(R^6)_2$, $SO_2NR^5R^6$, $SO_3R^6$, $C(O)R^5$, $C(O)OR^5$, $C(O)R^6$, $C(O)OR^6$, $NC(O)C(O)R^6$, $NC(O)C(O)R^5$, $NC(O)C(O)OR^6$, $NC(O)C(O)N(R^6)_2$, $C(O)N(R^6)_2$, $C(O)N(OR^6)R^6$, $C(O)N(OR^6)R^5$, $C(NOR^6)R^6$, $C(NOR^6)R^5$, $N(R^6)_2$, $NR^6C(O)R^1$, $NR^6C(O)R^6$, $NR^6C(O)R^5$, $NR^6C(O)OR^6$, $NR^6C(O)OR^5$, $NR^6C(O)N(R^6)_2$, $NR^6C(O)NR^5R^6$, $NR^6SO_2R^6$, $NR^6SO_2R^5$, $NR^6SO_2N(R^6)_2$, $NR^6SO_2NR^5R^6$, $N(OR^6)R^6$, $N(OR^6)R^5$, $P(O)(OR^6)N(R^6)_2$, and $P(O)(OR^6)_2$;
    each $R^5$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^5$ optionally comprises up to 3 substituents, each of which, if present, is $R^1$;
    each $R^6$ is independently selected from H, (C1–C4)-straight or branched alkyl, or (C2–C4)-straight or branched alkenyl; and each $R^6$ optionally substituted with R7;
    $R^7$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^7$ optionally comprises up to 2 substituents independently chosen from H, ($C_1$–$C_4$)-straight or branched alkyl, or ($C_2$–$C_4$) straight or branched alkenyl, 1,2-methylenedioxy, 1,2-ethylenedioxy, or $(CH_2)_n$—Z;

wherein n is 0, 1 or 2; and wherein if B is unsubstituted phenyl and all of said substituents present are on B' are $R^1$, then at least one of said $R^1$ substituents is not chloro, bromo or iodo; and wherein B and B' are not simultaneously unsubstituted phenyl.

2. The compound according to claim 1 having the formula:

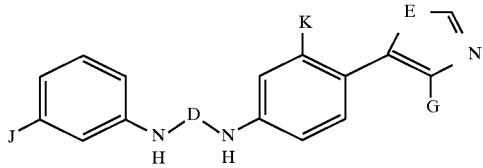

wherein:

K is selected from $R^1$ and $R^4$; and

J is selected from $R^1$, $R^2$, and $R^4$.

3. The compound according to claim 2, wherein J is $NR^6C(O)R^5$ or $NR^6C(O)R^6$.

4. The compound according to claim 3, wherein J is $NR^6C(O)R^6$.

5. The compound according to claim 4, wherein J is $N(CH_3)C(O)R^6$.

6. The compound according to claim 2, wherein K is $(CH_2)_n$—Y.

7. The compound according to claim 6, wherein K is $OCH_3$.

8. The compound according to claim 2, wherein G is hydrogen.

9. The compound according to claim 5, wherein:

K is $OCH_3$; and

G is hydrogen.

10. A pharmaceutical composition comprising:

a. a compound of the formula:

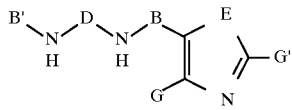

in an amount effective to inhibit IMPDH activity, wherein B, B', D, E, G and G' are as defined in claim 1;

b. an additional agent selected from an immunosuppressant, an anti-cancer agent, an anti-viral agent or an anti-vascular hyperproliferation agent; and c. a pharmaceutically acceptable adjuvant.

11. The composition according to claim 10, wherein in said compound, at least one B comprises at least a first substituent and wherein said first substituent is $R^5$.

12. A pharmaceutical composition comprising:

a. a compound according to any one of claims 1 to 9 in an amount effective to inhibit IMPDH activity; and b. a pharmaceutically acceptable adjuvant.

13. The pharmaceutical composition according to claim 12, additionally comprising an additional agent selected from an immunosuppressant, an anti-cancer agent, an anti-viral agent or an anti-vascular hyperproliferation agent.

14. A method for treating or preventing IMPDH mediated disease in a mammal comprising the step of administering to said mammal a composition according to claim 10.

15. A method for treating or preventing IMPDH mediated disease in a mammal comprising the step of administering to said mammal a composition according to claim 12.

16. The method according to claim 15, wherein said composition additionally comprises an agent selected from an immunosuppressant, an anti-cancer agent, an anti-viral agent or an anti-vascular hyperproliferation agent.

17. The method according to any one of claims 14 to 16, wherein said method is used to suppress an immune response and wherein said additional agent, if present, is an immunosuppressant.

18. The method according to claim 17, wherein said IMPDH mediated disease is an autoimmune disease.

19. The method according to any one of claims 14 to 16, wherein the IMPDH mediated disease is a viral disease and wherein said additional agent, if present, is an anti-viral agent.

20. The method according to any one of claims 14 to 16, wherein the IMPDH mediated disease is a vascular disease and wherein said additional agent, if present, is an anti-vascular hyperproliferation agent.

21. The method according to any one of claims 14 to 16, wherein the IMPDH mediated disease is cancer and wherein said additional agent, if present, is an anti-cancer agent.

* * * * *

UNITED STATES PATENT AND TRADEMARK OFFICE
CERTIFICATE OF CORRECTION

PATENT NO.    : 5,807,876
DATED         : September 15, 1998
INVENTOR(S)   : Armistead et al.

It is certified that error appears in the above-identified patent and that said Letters Patent is hereby corrected as shown below:

Title page,
Item [56], OTHER PUBLICATIONS, change "Demonstrations of Induction of Erythocyte Inosine Monophosphate Dehydrogenase Acitivity" to
-- Demonstration of Induction of Erythrocyte Inosine Monophosphate Dehydrogenase Activity --.

Column 5,
Line 63, change "maybe" to -- may be --.

Column 6,
Line 7, change "maybe" to -- may be --.
Line 21, change "0," to -- O, --.
Line 33, delete "be".
Line 60, change "Reaaents" to -- Reagents --.

Column 17,
Lines 10 and 64, change "including," to -- including --.

Column 18,
Line 66, change "non linear" to -- non-linear --.

Column 22,
Line 39, change "0.59" to -- 0.591 --.

Column 24,
Line 65, change "(d) 3.68" to -- (d) , 3.68 --.

Column 25,
Line 20, change "H" to -- $^1$H --.
Line 20, change "H" to -- $^1$H --.
Line 62, change "0.8" to -- 0.85 --.

Column 28,
Line 64, change "0.76" to -- 0.765 --.

Column 30,
Line 16, change "1H" to -- $^1$H --.
Line 40, change "Diluted" to -- The mixture was diluted --.
Line 41, change "KHSO$_{41}$" to -- KHSO$_4$, --.
Line 42, change "Redissolved" to -- The mixture was redissolved --.
Line 64, change "3MM" to -- 3mM --.

UNITED STATES PATENT AND TRADEMARK OFFICE
CERTIFICATE OF CORRECTION

PATENT NO. : 5,807,876
DATED : September 15, 1998
INVENTOR(S) : Armistead et al.

It is certified that error appears in the above-identified patent and that said Letters Patent is hereby corrected as shown below:

<u>Column 32,</u>
Line 59, change "maybe" to -- may be --.

<u>Column 33,</u>
Line 3, change "maybe" to -- may be --.
Line 10, insert
-- Z is selected from halogen, CN, $NO_2$, $CF_3$, $OCF_3$, OH, $S(C_1-C_4)$-alkyl, SO $(C_1-C_4)$-alkyl, $SO_2$ $(C_1-C_4)$-alkyl, $NH_2$, NH $(C_1-C_4)$-alkyl, N $((C_1-C_4)$ - alkyl$)_2$, $N((C_1-C_4)$-alkyl$)R^8$, COOH, $C(O)O(C_1-C_4)$-alkyl or $O(C_1-C_4)$-alkyl; and
$R^8$ is an amino protecting group; and
wherein any carbon atom in any A, $R^2$ or $R^6$ is optionally replaced by O, S, SO, $SO_2$, NH, or $N(C_1-C_4)$-alkyl. -- before
"wherein if B is unsubstituted phenyl and all of".

Signed and Sealed this

Twelfth Day of August, 2003

JAMES E. ROGAN
*Director of the United States Patent and Trademark Office*